US00PP37187P2

(12) United States Plant Patent
Hansen

(10) Patent No.: US PP37,187 P2
(45) Date of Patent: Dec. 30, 2025

(54) ***EPIMEDIUM* PLANT NAMED 'Jester's Hat'**

(50) Latin Name: ***Epimedium* hybrid**
Varietal Denomination: Jester's Hat

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,788

(22) Filed: Sep. 9, 2025

Related U.S. Application Data

(60) Provisional application No. 63/732,731, filed on Sep. 13, 2024.

(51) Int. Cl.
*A01H 6/00* (2018.01)
*A01H 5/00* (2018.01)
*A01H 5/02* (2018.01)

(52) U.S. Cl.
USPC ..... Plt./429
CPC ..... *A01H 6/00* (2018.05); *A01H 5/00* (2013.01); *A01H 5/02* (2013.01)

(58) Field of Classification Search
USPC ..... Plt./429
CPC ..... A01H 6/00; A01H 5/02
See application file for complete search history.

*Primary Examiner* — Keith O. Robinson

(57) ABSTRACT

A new cultivar of *Epimedium* plant named 'Jester's Hat' characterized by its medium size habit, evergreen foliage. The flowers are golden yellow spurs with reddish sepals on airy branched corymbs beginning in late spring. The foliage has three leaflets of light chartreuse with large segments of reddish in cooler conditions and becoming deep green in summer.

2 Drawing Sheets

Botanical denomination: *Epimedium* hybrid.
Variety designation: 'Jester's Hat'.

STATEMENT REGARDING PRIOR DISCLOSURES UNDER 37 CFR 1.77(B)(6)

The Applicant asserts that no publications or advertisements relating to sales, offers for sale, or public distribution occurred more than one year prior to the effective filing date of this application. The first offer for sale was by Walters Gardens, Inc. to Pleasant Run Nursery on Sep. 15, 2023. Subsequently, on Feb. 1, 2024, a photo and brief description of the new plant was posted on a website hosted by Walters Gardens, Inc. Walters Gardens, Inc. obtained the new plant and all information about the new plant directly from the inventor. Any information or disclosure about the claimed plant less than one year prior to the effective filing date of this application would have been obtained from directly or indirectly from the Inventor and would be a 35 U.S.C. 102(b) exception.

BACKGROUND OF THE INVENTION

The present invention relates to a new and distinct Barrenwort plant from the genus *Epimedium* and given the cultivar name 'Jester's Hat'. The new plant was the result of a single seedling selection from a cross on Apr. 30, 2014, by the inventor between 'Amber Queen' U.S. Plant Pat. No. 17,197 as the female or seed parent and *Epimedium* x *omeiense* 'Rigoletto' (not patented) as the male or pollen parent. The seeds from the pollination were collected in May of 2014. The individually selected seedling was eventually given the breeder code 14-3-14 after being first isolated from trials at a nursery in Zeeland, MI during April of 2016. It was selected for the final introduction in April of 2019.

*Epimedium* 'Jester's Hat' has been asexually propagated at the same nursery in Zeeland, MI originally by division of the rhizome in 2016 and found to reproduce plants that are identical and exhibit all the characteristics of the original plant in successive generations of asexual propagation.

*Epimedium* 'Jester's Hat' has not been observed under all possible environments. The phenotype may vary slightly with different environmental conditions, such as temperature, light, fertility, moisture and maturity levels, but without any change in the genotype.

In comparison to the new plant, the female parent has smaller flowers of yellowish spurs with yellow sepals. The male parent has more ovate foliage with narrower apex and the flower spurs are more reddish and less orange with fewer flowers per stem and is less floriferous.

The nearest comparison varieties known to the inventor are: 'Cranberry Dancer' U.S. Plant Pat. No. 36,548 and 'Dream Catcher' U.S. Plant Pat. No. 36,549.

'Cranberry Dancer' has flowers with yellowish spur tips and burgundy spur bases with larger sepals of burgundy centers and white margins. 'Dream Catcher' has a similar habit in both height and width but has flowers with a brighter golden-yellow spurs with more reddish sepals.

*Epimedium* 'Jester's Hat' is distinct from the parents and all other *Epimedium* known to the inventor in the following combined traits:

1. Medium-sized, dense, evergreen perennial;
2. Medium-sized with bright golden-yellow spurs and orangish-red sepals on airy branched panicles beginning in late spring;
3. Foliage has three leaflets, light chartreuse strong wine-coloration in cooler conditions becoming medium green in the heat of summer.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source, and direction may cause the appearance of minor variations in color.

DETAILED PLANT DESCRIPTION

Figure 1:
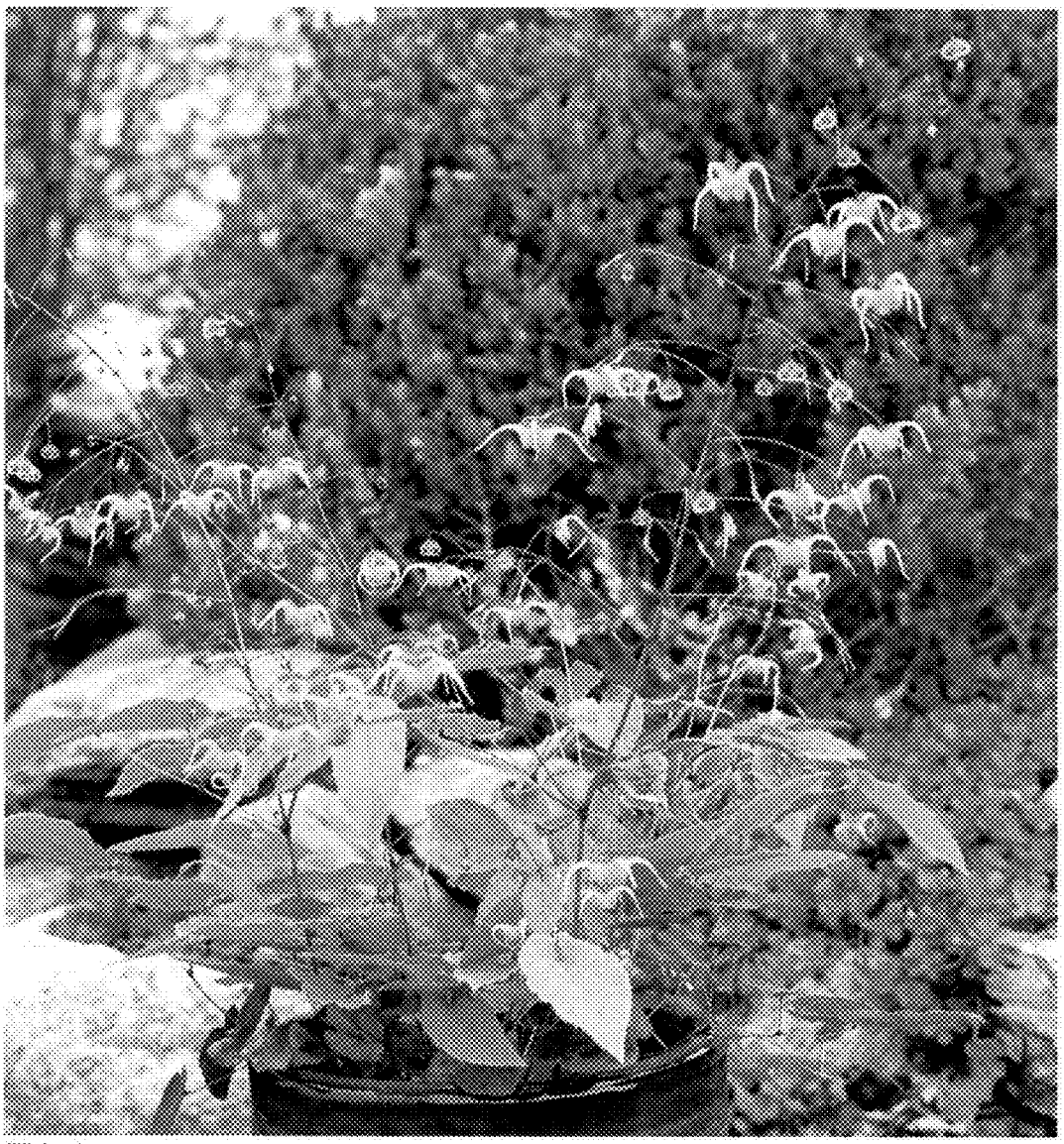
FIG. 1 shows a container of a two-year-old plant in mid-season flower from a greenhouse grown specimen at a nursery near Zeeland, Michigan.
Figure 2:
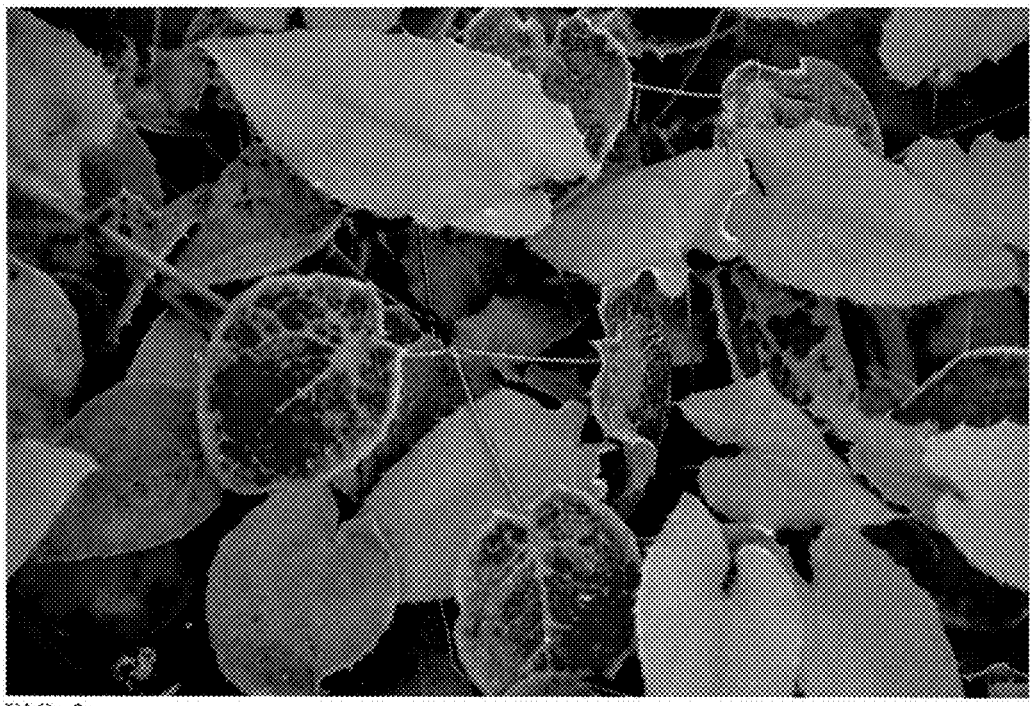
FIG. 2 shows a close-up of a leaf with burgundy patterns in early spring.
Figure 3:
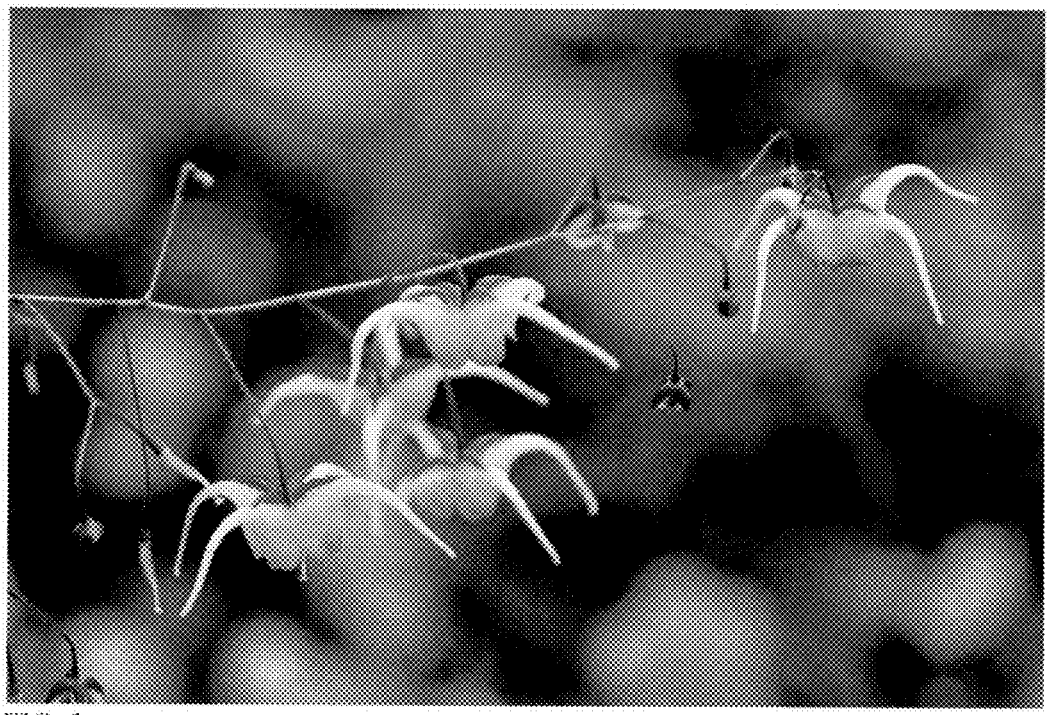
FIG. 3 shows a close-up of the scapes with flowers and buds.

The following is a detailed description of the new *Epimedium* cultivar 'Jester's Hat' based on observations of a three-year-old specimen grown with supplemental watering and fertilizer as needed in a display garden at a wholesale perennial nursery in Zeeland, MI. Color descriptions are from the 2015 edition of The Royal Horticultural Society Colour Chart except where common dictionary terms are used.

Parentage: The female or seed parent is 'Amber Queen' U.S. Plant Patent No. 17,197, the male or pollen parent is 'Rigoletto' (non-patented);

Propagation: Rhizome divisions;

Crop time: Finishing in a 3.8-liter pot from a 50 mm plug in 10 to 12 weeks;

Growth rate: Moderate;

Root development: Initiating in about 6 weeks;

Crop time: Finishing in a 3.8-liter pot from a 50 mm plug in 10 to 12 weeks;

Plant size: Soil level to top of foliar plane to about 44 cm tall and to about 90 cm wide, soil level to top of floral plane about 55 cm;

Root description: Dense, fibrous roots on rhizomes;

Rhizomes: Surface smooth, matte, glabrous; about 3.5 cm in length and 5 mm in width; color nearest RHS 164A;

Branching habit: Branches arise from rhizome;

Stem: Cylindrical; moderately glossy, glabrous; strong; stiff; to about 36 cm in length and 2 mm in diameter at base;

Stem color: Variable, nearest RHS 181C and between RHS 51D and RHS 37C; nodes between RHS 187A and RHS 176A;

Stem aspect: Initially upright and arching with maturity;

Internode length: 36 cm;

Leaf: Typically one or two tri-parted leaf per node; to 16 cm wide and 15 cm long;

Leaflet: Three; oblong ovate; stiff; acute apex; cordate base not overlapping; flat to slightly convex; finely serrulate with stiff, sharply-pointed, small spines variably in size from 1 mm to 2 mm wide and 1 mm to 2 mm in length; center leaflet to 10 cm long and 4.5 cm wide; side leaflets to 10 cm long and 4.2 cm wide;

Leaflet surface: Adaxial smooth, glabrous, moderately lustrous; abaxial smooth, glabrous, matte;

Leaflet color: Young expanding adaxial between RHS 143C and RHS 144B with irregular blotches of between RHS 172C and RHS 165C, young expanding abaxial nearest RHS 147C with a light overtone of nearest RHS 178B; mature adaxial nearest RHS 137C, mature abaxial nearest N138C;

Leaflet venation: Pinnate; adaxial lightly indented; abaxial slightly costate;

Vein color: Adaxial nearest RHS 146D and abaxial midrib and primary veins nearest RHS 147C with variable blush of nearest RHS 180A;

Petioles: Arising from rhizome; cylindrical; smooth; slightly lustrous; wiry; to 36 cm long and 2 mm diameter;

Petiole color: RHS 51D and RHS 37C;

Petiolules: Cylindrical; smooth; slightly lustrous; stiff; to about 6.5 cm long and 1 mm diameter on center leaflets and to about 5 cm long and 0.8 mm diameter on side leaflets;

Petiolule color: Emerging foliage nearest RHS 187B maturing to between RHS 180A and RHS 179B;

Inflorescence: Compound corymb; flowering in the upper 30 cm and to about 28 cm wide; with about 22 branches, branches having to about 10 flowers; inflorescence with about 75 flowers;

Flower buds one day prior to starting to open: Globose; smooth, glabrous, about 4 mm long and 5 mm diameter;

Bud color one day prior to starting to open: Sepals nearest RHS 59A;

Flower: Perfect; complete; actinomorphic;

Flower size: To about 32 mm in diameter and 15 mm in depth;

Flower fragrance: None detected;

Lastingness of flowers: About 7 days from initial opening dehiscence; self-cleaning;

Petals: Four; spurs; lanceolate; arcuate outwardly and curving toward center axis; apex narrowly acute; base truncate, adnate on axial portion; adaxial and abaxial smooth, glabrous and slightly lustrous; to about 18 mm long natural, 22 mm long straightened, and about 5 mm across at opening;

Petal color: When opening and fully open spur adaxial and abaxial nearest RHS 175B along lowest edge transitioning to nearest RHS 4B with a blush of RHS 175B decreasing distally, with apical 1 mm nearest RHS 14B, and the tissue between the base of the spur and the apex between RHS 9B and RHS 9C;

Pedicel: Cylindrical; puberulent to micro-glandular; to about 26 mm long and 0.3 mm diameter; average about 15 mm long and 0.3 mm diameter at base;

Pedicel color: Distally between RHS 146A and RHS NN137C, proximally between RHS 146C and RHS 146B;

Peduncle: Cylindrical; stiff; strong; glabrous to sparsely puberulent; slightly lustrous; with to about 22 branches; main peduncle aspect upright to arching; proximal branches outwardly to about 60 degrees from main axis and distal branches to about 80 degrees from main axis; flowering in the distal 30 cm long and 28 cm diameter; branches to about 14.5 cm long and 1.5 mm diameter at base;

Peduncle color: Proximal portion nearest RHS 146D moderately to heavily maculate with nearest RHS 183C, distal portion and branches between RHS 146C and RHS 146B, with branch nodes between RHS 147B and RHS 146A;

Sepals: Four; rotate; single whorl; lanceolate; smooth, glabrous and matte; attenuate base, acute apex; margin entire; to about 7 mm long and 3 mm across;

Sepal color: Adaxial and abaxial 1 mm base nearest RHS 145D, adaxial distal 6 mm nearest RHS 59C, and abaxial distal 6 mm between RHS 59C and RHS 59D;

Androecium: Four;

*Anther*.—Four; longitudinal; basifixed; extrose; oblong; to about 1.5 mm long and 1 mm across; color prior to opening nearest RHS 8B.

*Filaments*.—Four; applanate; about 4 mm long and 1 mm wide at base, narrowing distally; color nearest RHS 3B.

*Pollen*.—Abundant; color nearest RHS 9A.

Gynoecium: Single; superior;

*Style*.—Cylindrical; glabrous; about 2.5 mm long and 0.3 mm diameter; color between RHS 146D and RHS 145C.

*Stigma*.—Oblong; glabrous; to about.05 mm long and about 0.5 mm diameter; color nearest RHS 145C.

*Ovary*.—Oblong; glabrous; smooth; to about 3 mm long and 1 mm diameter; color nearest RHS 144A.

Gynoecium: Single; superior; consisting of style, stigma, and ovary;

Resistance: Not been tested or shown to be susceptible or resistance to pests and diseases common to *Epimedium;*

Hardiness: The new plant has survived USDA winter hardiness to at least zones 5 to 8 but has not been tested yet beyond these temperatures.

It is claimed:

1. A new and distinct cultivar of *Epimedium* plant named 'Jester's Hat' as herein described and illustrated.

* * * * *